US006329530B1

(12) United States Patent
Maywald et al.

(10) Patent No.: US 6,329,530 B1
(45) Date of Patent: Dec. 11, 2001

(54) METHOD FOR THE PRODUCTION OF 1-SUBSTITUTED 5-HYDROXYPYRAZOLES

(75) Inventors: Volker Maywald, Ludwigshafen; Adrian Steinmetz, Mannheim; Michael Rack, Heidelberg; Norbert Götz, Worms; Roland Götz, Neulussheim; Jochem Henkelmann, Mannheim; Heike Becker, Limburgerhof; Juan Jose Aiscar Bayeto, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/830,948

(22) PCT Filed: Nov. 6, 1999

(86) PCT No.: PCT/EP99/08515

§ 371 Date: May 3, 2001

§ 102(e) Date: May 3, 2001

(87) PCT Pub. No.: WO00/31041

PCT Pub. Date: Jun. 2, 2000

(30) Foreign Application Priority Data

Nov. 19, 1998 (DE) .............................. 198 53 501

(51) Int. Cl.[7] .............................. C07D 231/20

(52) U.S. Cl. .................... 548/366.1; 548/370.4

(58) Field of Search .............. 548/366.1, 370.4

(56) References Cited

U.S. PATENT DOCUMENTS

| 4,256,902 | * | 3/1981 | Boschi et al. ............... 548/365 |
| 4,643,757 | | 2/1987 | Baba et al. . |
| 4,744,815 | | 5/1988 | Baba et al. . |
| 5,543,568 | | 8/1996 | Henkelmann et al. . |
| 5,607,898 | | 3/1997 | Nakamura et al. . |

(List continued on next page.)

FOREIGN PATENT DOCUMENTS

| 2214854 | 10/1996 | (CA) . |
| 240 001 | 10/1987 | (EP) . |
| 587 072 | 3/1994 | (EP) . |
| 837 058 | 4/1998 | (EP) . |
| 970 956 | 1/2000 | (EP) . |

(List continued on next page.)

OTHER PUBLICATIONS

83–823274/47 Dewent.
Chem.Ber.1976,109,S.261.
Dewent 86261531.
Dewent 87–010930/02.

(List continued on next page.)

Primary Examiner—Robert W. Ramsuer
Assistant Examiner—Kamal Saeed
(74) Attorney, Agent, or Firm—Keil & Weinkauf

(57) ABSTRACT

The invention relates to a method for the production of 1-substituted 5-hydroxypyrazoles of formula (I) wherein $R^1$ is $C_1$–$C_6$-alkyl, $C_2$–$C_6$-alkenyl, $C_2$–$C_6$-alkinyl, $C_3$–$C_6$-cycloalkyl or $C_1$–$C_4$-alkoxy, whereby these groups can be substituted by halogen, $C_1$–$C_4$-alkoxy, phenoxy, $C_1$–$C_6$-alkoxycarbonyl, $C_1$–$C_6$-alkylthiocarbonyl or a cyclic ring system with 3–14 ring atoms, by reacting a) an alkylvinylether of general formula (III) wherein $R^2$ is $C_1$–$C_6$-alkyl or $C_3$–$C_6$-cycloalkyl, with phosgene (IVa), "diphosgene" (IVb) or "triphosgene" (IVc) to form acid chlorides of formula (V), b) transforming said acid chlorides by eliminating hydrogen chloride into the corresponding 3-alkoxyacrylic acid chloride of formula (VI) and c) reacting said acid chloride with hydrazines of formula (VII) wherein $R^1$ has the above cited meaning, to form 5-hydroxypyrazoles of formula (I).

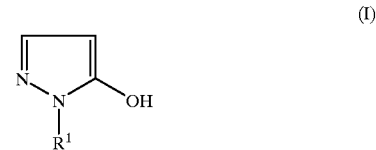

(I)

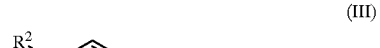

(III)

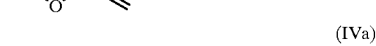

(IVa)

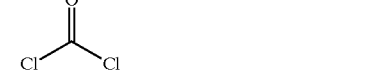

(IVb)

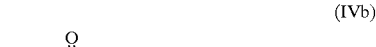

(IVc)

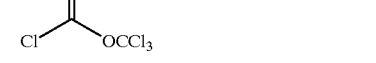

(V)

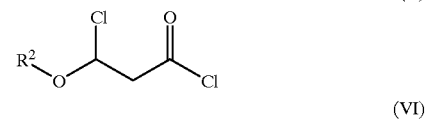

(VI)

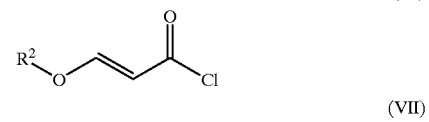

(VII)

7 Claims, No Drawings

U.S. PATENT DOCUMENTS

| | | |
|---|---|---|
| 5,631,210 | 5/1997 | Tseng . |
| 5,723,408 | 3/1998 | Shibata . |
| 5,808,092 * | 9/1998 | Mizutare et al. ................ 548/366.1 |
| 5,846,907 | 12/1998 | VonDeyn et al. . |
| 5,863,866 | 1/1999 | Tseng . |
| 5,952,266 | 9/1999 | Tseng . |
| 5,985,799 | 11/1999 | Tseng . |

FOREIGN PATENT DOCUMENTS

| | | |
|---|---|---|
| 58-140074 | 8/1958 | (JP) . |
| 61-189271 | 8/1961 | (JP) . |
| 61-229852 | 10/1961 | (JP) . |
| 61-268659 | 11/1961 | (JP) . |
| 58-140073 | 8/1983 | (JP) . |
| 58-174369 | 10/1983 | (JP) . |
| 60-51175 | 3/1985 | (JP) . |
| 61-257974 | 11/1986 | (JP) . |
| 6-166666 | 6/1994 | (JP) . |
| 96/25412 | 8/1996 | (WO) . |
| 96/26206 | 8/1996 | (WO) . |
| 96/30368 | 10/1996 | (WO) . |
| 96/31507 | 10/1996 | (WO) . |
| 97/01550 | 1/1997 | (WO) . |
| 87/08164 | 3/1997 | (WO) . |
| 97/23135 | 3/1997 | (WO) . |
| 97/12885 | 4/1997 | (WO) . |
| 97/19087 | 5/1997 | (WO) . |

OTHER PUBLICATIONS

83–773699/39 Dewent.
Annalen 1965,686,134–144.
Dewent 94–230645/28.
J.Prakt.Chem. 1971, 313, 115–128.
J.Prakt.Chem. 1971, 313, 1118–1124.
DewentAbst. 85–107397/18.
DewentAbst.97–363315/33.
DewentAbst. 96–068643/07.

* cited by examiner

METHOD FOR THE PRODUCTION OF 1-SUBSTITUTED 5-HYDROXYPYRAZOLES

This application is a 371 of PCT/EP 99/08515 filed November 1999.

The present invention relates to a process for preparing 1-substituted 5-hydroxypyrazoles of the formula I

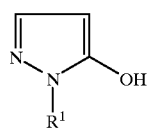

in which $R^1$ is $C_1$–$C_6$-alkyl, $C_2$–$C_6$-alkenyl, $C_2$–$C_6$-alkynyl, $C_3$–$C_6$-cycloalkyl or $C_1$–$C_4$-alkoxy, where these groups may be substituted by halogen, $C_1$–$C_4$-alkoxy, phenoxy, $C_1$–$C_6$-alkoxycarbonyl, $C_1$–$C_6$-alkylthiocarbonyl or by a cyclic ring system having 3–14 ring atoms.

1-Substituted 5-hydroxypyrazoles are used as intermediates for preparing pharmaceutics and crop protection agents, in particular herbicides, and are disclosed, for example, in WO 96/26206, WO 97/23135, WO 97/19087, U.S. Pat. No. 5,631,210, WO 97/12885, WO 97/08164, ZA 9510980, WO 97/01550, WO 96/31507, WO 96/30368 and WO 96/25412.

Processes for their preparation are therefore of interest.

To date, the following syntheses are known as processes for preparing lower 1-alkyl-5-hydroxypyrazoles:
1. a preparation where 2-methyl-1-(p-toluenesulfonyl)-3-pyrazolidone or 2-methyl-1-acetylpyrazolidone is hydrolyzed (J. Prakt. Chem. 313 (1971), 115–128 and J. Prakt. Chem. 313 (1971), 1118–1124).
2. a variant in which alkyl 5-hydroxy-1-alkylpyrazole-4-carboxylate is synthesized by cyclization of a dialkyl alkoxymethylenemalonate with lower alkylhydrazines, an aqueous solution of mineral acid is subsequently added to this reaction product and hydrolysis and decarboxylation are carried out simultaneously (see JP 61257974, JP 60051175, JP 58174369, JP 58140073 and JP 58140074 and also U.S. Pat. No. 4,643,757).
3. a synthesis in which ethyl propiolate is reacted with methylhydrazine to give 5-hydroxy-1-methylpyrazole (Annalen 686 (1965), 134–144).
4. a synthesis route in which 3-hydrazinopropionic esters, which are formed by addition of hydrazine to acrylic esters, are reacted with aldehydes to give the corresponding hydrazones, which are subsequently cyclized (see JP 06166666, JP 61229852 and JP 61268659 and also EP 240001).
5. a synthesis variant in which a 5-hydroxy-1-methylpyrazole-3-carboxylic acid is cleaved thermally (Chem. Ber. 109 (1976), 261).
6. a process in which 3-alkoxyacrylic esters are reacted with methylhydrazine and ethylhydrazine to give 1-methyl-5-hydroxypyrazole and 1-ethyl-5-hydroxypyrazole, respectively (see JP 189 271/86, EP-A-837 058).

The process of the 1st synthesis route mentioned above entails several steps and is complicated. Introduction and removal of a protecting group is awkward, means an additional number of steps and reduces the yield.

The 2nd preparation possibility entails several steps; moreover, in addition to the 1-alkyl-5-hydroxypyrazoles, the regioisomers of the target compound are formed at the same time, and they have to be separated off from the target compounds in a complicated procedure. Furthermore, the synthesis is associated with a poor C yield since a C4 building block is employed from which, at the end of the process, a carbon atom has to be cleaved off again.

In the 3rd synthesis variant, which describes only the preparation of 1-methyl-5-hydroxypyrazole, it is unavoidable to employ highly hyperstoichiometric amounts of methylhydrazine, thus rendering the process uneconomical. In addition, the isomer 3-hydroxy-1-methylpyrazole, which is also formed, has to be separated off from 1-methyl-5-hydroxypyrazole in a complicated procedure during purification. Furthermore, owing to the high cost of propiolic ester, this process is uneconomical.

The process of the 4th alternative entails several steps and is complicated. The last step of the complex process affords only poor yields and a large number of byproducts.

The thermal cleavage of the 5th synthesis route requires a high temperature, and the yield of 6% is very low.

The 6th synthesis route, which describes only the preparation of 1-methyl-5-hydroxypyrazole, uses 3-alkoxyacrylic esters which are difficult to prepare and are expensive. The preparation of 3-alkoxyacrylic esters is carried out by reaction of methanol with expensive propiolic esters (Tetrahedron Lett. 24 (1983), 5209, J. Org. Chem. 45 (1980), 48, Chem. Ber. 99 (1966), 450, Chem. Lett. 9 (1996), 727–728), by reacting α,α-dichlorodiethyl ether, which is expensive and difficult to synthesize, with bromoacetic esters (Zh. Org. Khim. 22 (1986), 738), by reaction of bromoacetic esters with trialkyl formates (Bull. Soc. Chim. France N 1–2 (1983), 41–45) and by elimination of methanol from 3,3-dialkoxypropionic esters (DE 3701113) (obtainable by reacting the expensive methyl propiolate with methanol (J. Org. Chem. 41 (1976), 3765)), by reacting 3-N-acetyl-N-alkyl-3-methoxypropionic esters with methanol (J. Org. Chem. 50 (1985), 4157–4160, JP 60-156643), by reacting acrylic esters with alkylamines and acetic anhydride (J. Org. Chem. 50 (1985), 4157–4160), by reacting ketene with trialkyl orthoformate (DK 158462), by palladium- and simultaneously copper-catalyzed reaction of acrylic esters with methanol (DE 4100178.8), by reaction of trichloroacetyl chloride with vinyl ethyl ether (Synthesis 4 (1988), 274), by reacting α,α,α-trichloro-β-methoxybuten-2-one with methanol (Synthesis 4 (1988), 274) and by reacting the sodium salts of 3-hydroxyacrylic esters with alcohols (DB 3641605). The fact that the 3-alkoxyacrylic esters are difficult to obtain thus renders the synthesis according to 6. uneconomical. Moreover, JP 189 271/86 only describes the isolation of the 5-hydroxy-1-methylpyrazole as the hydrochloride, but no details are given for the isolation and purification of the free base. Efforts to apply the reaction conditions described in JP 189 271/86 and to isolate the free base result in only very 35 poor yields which are uneconomical for a preparation of hydroxypyrazoles on an industrial scale. EP-A 837 058 only discloses the preparation of 5-hydroxy-1-ethylpyrazole.

Consequently, these synthesis routes are not satisfactory as economical and efficient processes for preparing 1-substituted-5-hydroxypyrazoles. This is particularly true for the industrial preparation of the 1-substituted 5-hydroxypyrazoles in large amounts.

It is an object of the present invention to provide an alternative preparation process for preparing 1-substituted 5-hydroxypyrazoles which does not have the abovementioned disadvantages of the prior art processes.

We have found that this object is achieved by the process according to the invention for preparing 1-substituted 5-hydroxypyrazoles of the formula I

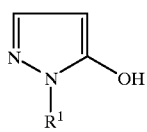

in which $R^1$ is $C_1$–$C_6$-alkyl, $C_2$–$C_6$-alkenyl, $C_2$–$C_6$-alkynyl, $C_3$–$C_6$-cycloalkyl or $C_1$–$C_4$-alkoxy, where these groups may be substituted by halogen, $C_1$–$C_4$-alkoxy, phenoxy, $C_1$–$C_6$-alkoxycarbonyl, $C_1$–$C_6$-alkylthiocarbonyl or by a cyclic ring system having 3–14 ring atoms, by a) reacting an alkyl vinyl ether of the formula III

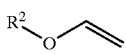

in which $R^2$ is $C_1$–$C_6$-alkyl or $C_3$–$C_6$-cycloalkyl with phosgene IVa, "diphosgene" IVb or "triphosgene" IVc

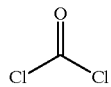

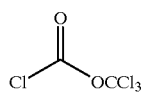

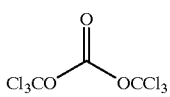

to give acyl chlorides of the formula V

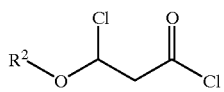

b) converting these by elimination of hydrogen chloride into the corresponding 3-alkoxyacryloyl chloride of the formula VI

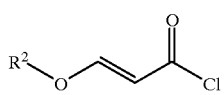

and
c) reacting this with hydrazines of the formula VII

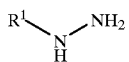

in which $R^1$ is as defined above to give 5-hydroxypyrazoles of the formula I.

Preferred embodiments of the process according to the invention are shown in the subclaims and in the description below.

Step a):

The process according to the invention starts with alkyl vinyl ethers of the formula III which are initially reacted at from −78° C. to 100° C., preferably from −10° C. to 80° C., in particular from 20° C. to 60° C., with an acyl chloride of the formula IVa, IVb or IVc, to give the corresponding acyl chloride of the formula V.

The reaction can be carried out without using solvents or diluents if the reaction partners are liquid at the reaction temperature. However, it is also possible to carry out the reaction in an aprotic solvent or diluent.

Suitable solvents or diluents are, for example, aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, and also ethers, such as diethyl ether, diisopropyl ether, tert-butyl methyl ether, dioxane, anisole and tetrahydrofuran, and nitrites, such as acetonitrile and propionitrile. It is of course also possible to use mixtures of the abovementioned solvents.

Particularly preferably, the reaction is carried out in the absence of a solvent, or in aromatic hydrocarbons such as toluene as solvent.

The reaction partners III and IV are generally reacted with each other in a ratio of from 0.1:1 to 1:1 mol of III/IVa, IVb or IVc, preferably from 0.2:1 to 0.8:1 mol of III/IVa, IVb or IVc, in particular from 0.4:1 to 0.6:1 mol of III/IVa, IVb or IVc.

Since both the halides IV and the acyl chloride V which is formed are unstable toward moisture, it is recommended to carry out the reaction under exclusion of water, preferably under an atmosphere of protective gas (nitrogen or another inert gas).

In the case of the reaction of III with IVb or IVc, it may be advantageous to accelerate the reaction by addition of catalytic amounts of a tertiary amine, such as triethylamine or pyridine.

Step b):

At 30–80° C., the resulting acyl chloride V eliminates hydrogen chloride (HCl), giving the corresponding 3-alkoxyacryloyl chloride VI. The preparation of this acyl chloride VI is described in EP-A 0 587 072.

For this step of the reaction, it may be advantageous to remove the hydrogen chloride which has formed from the reaction volume, by applying slightly reduced pressure or by passing inert gas through the reaction mixture or the reaction vessel, thus removing the hydrogen chloride which has formed.

The excess chloride of the formula IVa, IVb or IVc can be recycled into the synthesis and has to be removed in any case for the isolation of the pure product of value. This also applies to any catalysts which may have been added.

The resulting crude 3-alkoxyacryloyl chlorides VI can be isolated in pure form by distillation or rectification.

However, they can also be further used directly, without further purification.

Step c):

The reaction of the 3-alkoxyacryloyl chlorides of the formula VI with hydrazines of the formula VII to give 1-substituted 5-hydroxypyrazoles is generally carried out such that the hydrazine VII is initially charged in an organic solvent at from −20 to 80° C., preferably from −20° C. to 50° C., and the acyl chloride VI is added dropwise over a period of 0.2–3 h.

Suitable solvents or diluents are, for example, aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, and also ethers, such as diethyl ether, diisopropyl ether, tert-butyl methyl ether, dioxane, anisole and tetrahydrofuran, and nitriles, such as acetonitrile and propionitrile. It is of course also possible to use mixtures of the abovementioned solvents.

To cyclize the hydrazide which is formed, an organic or inorganic acid is added and the reaction mixture is heated to 30–100° C.

Suitable organic or inorganic acids are trifluoromethanesulfonic acid, p-toluenesulfonic acid, sulfuric acid, hydrochloric acid, phosphoric acid. Particular preference is given to using mineral acids, such as sulfuric acid and hydrochloric acid.

With respect to the intended use of the 1-substituted 5-hydroxypyrazoles of the formula I, the following radicals are suitable substituents:

$R^1$ $C_1$–$C_4$-alkyl, such as methyl, ethyl, n-propyl, 1-methylethyl, butyl, 1-methylpropyl, 2-methylpropyl and 1,1-dimethylethyl;

$C_1$–$C_6$-alkyl, such as $C_1$–$C_4$-alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2imethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

in particular methyl, ethyl, 1-methylethyl, 1-methylpropyl, 2-methylpropyl, 1,1-dimethylethyl and 1,1-dimethylpropyl;

$C_2$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl, 2-methyl-4-butenyl, 3-methyl-3-butenyl, 1,1-dimethyl-2-propenyl,1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3 pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and ethyl-2-methyl-2-propenyl, in particular 1-methyl-2-propenyl, 1-methyl-2-butenyl, 1,1-dimethyl-2-propenyl and 1,1-dimethyl-2-butenyl;

$C_2$–$C_6$-alkynyl, such as propargyl, 2-butynyl, 3-butynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

$C_3$–$C_6$-cycloalkyl, such as, for example, cyclopropyl, cyclobutyl, cyclopentyl and cyclohexyl, in particular cyclopropyl and cyclohexyl;

$C_1$–$C_4$-alkoxy, such as methoxy, ethoxy, n-propoxy, 1-methylethoxy, n-butoxy, 1-methylpropoxy, 2-methylpropoxy and 1,1-dimethylethoxy, in particular $C_1$–$C_3$-alkoxy, such as methoxy, ethoxy, isopropoxy;

where these groups may be unsubstituted or substituted by one to five halogen atoms, such as fluorine, chlorine, bromine and iodine, preferably fluorine and chlorine, $C_1$–$C_4$-alkoxy, phenoxy, $C_1$–$C_6$-alkoxycarbonyl, $C_1$–$C_6$-alkylthiocarbonyl or a cyclic ring system having 3–14 ring atoms, where the substituents are as defined below:

$C_1$–$C_6$-alkoxycarbonyl, such as methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl and 1,1-dimethylethoxycarbonyl, in particular methoxycarbonyl;

$C_1$–$C_6$-alkylthiocarbonyl, such as methylthiocarbonyl, ethylthiocarbonyl, n-propylthiocarbonyl, in particular methylthiocarbonyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

A cyclic ring system having 3–14 ring atoms means, for example, the following groups: $C_3$–$C_{14}$-cycloalkyl, $C_3$–$C_{14}$-cycloalkenyl, aromatic groups, such as phenyl, naphthyl, and their partially hydrogenated derivatives. The cyclic ring systems may furthermore represent heterocyclic ring systems in which one, two or three carbon atoms may be replaced by heteroatoms, such as, for example, O, N, S. In principle, the cyclic ring systems may be aromatic or partially or fully hydrogenated. The cyclic ring systems can be substituted at will. Suitable substituents are, for example, $C_1$–$C_6$-alkyl, $C_1$–$C_4$-haloalkyl, $C_1$–$C_4$-alkoxy, halogen, cyano, nitro, hydroxyl, thionyl, sulfoxyl, sulfonyl, $C_1$–$C_4$-alkylsulfonyl, amino, $C_1$–$C_4$-alkylamino and di-$C_1$–$C_4$-alkylamino.

Preference is given to cyclic ring systems from the group consisting of $C_1$–$C_6$-cycloalkyl, phenyl, a 5- to 6-membered heterocyclic, saturated or unsaturated radical containing one to three heteroatoms selected from the group consisting of O, N and S, each of which may be substituted as mentioned above.

Particular preference is given to $C_1$–$C_6$-cycloalkyl and phenyl which may be substituted as mentioned above.

A very particularly preferred cyclic ring system is phenyl which may be substituted as mentioned above.

$R^2$, $R^3$ independently of one another are $C_1$–$C_6$-alkyl as mentioned above or $C_3$–$C_6$-cycloalkyl, preferably $C_1$–$C_6$-alkyl.

EXAMPLES

Example 1

3-Ethoxyacryloyl Chloride

At 35° C., 110 g (1.1 mol) of phosgene are introduced into a solution of 72 g (1 mol) of ethyl vinyl ether in 100 g of toluene over a period of 1.5 h. The mixture is subsequently stirred at 60° C. for 4 hours. During the entire reaction time, phosgene and ethyl vinyl ether are recondensed into the reaction mixture using a dry-ice condenser at −78° C. The solution is subsequently stripped of phosgene at room temperature, and the solvent is removed by distillation. vacuum distillation at 36° C./0.4 mbar gives 88 g (66%) of the product of value.

Example 2

Isobutoxyacryloyl Chloride 100 g (1 mol) of isobutyl vinyl ether are initially charged in a 2 l stirred apparatus and heated to 50–55° C. 1024 g (10.4 mol) of phosgene are subsequently introduced over a period of 21 h, and 900 g (9 mol) of isobutyl vinyl ether are added dropwise over a period of 19 h. After an extra reaction time of 0.5 hours, the reaction mixture is heated to 80° C. with nitrogen stripping to eliminate hydrogen chloride. The low-boilers are then distilled off via a 15 cm Vigreux column, and the residue is analyzed by is gas chromatography. This gives 1364 g (70%) of crude isobutoxyacryloyl chloride (calc. 100%).

Example 3

3-Cyclohexyloxyacryloyl Chloride 50 g (0.5 mol) of phosgene are condensed into a stirred apparatus fitted with −78° C.-cooling. Over a period of 3 hours, 50.5 g (0.4 mol) of cyclohexyl vinyl ether are subsequently added dropwise at 20° C. The mixture is then stirred at 50° C. for 5 hours. The excess phosgene is flushed out with nitrogen, and the crude product is worked up by distillation. At 110° C./2.5 mbar, 66.4 g (88%) of the product of value were obtained.

Example 4

5-Hydroxy-1-methylpyrazole from 3-isobutoxyacryloyl Chloride and Monomethylhydrazine (1.8% strength)

In a 6 l flask, 2377 g of an aqueous monomethylhydrazine solution (0.93 mol) are initially charged at 10° C. A pH of 7 is established by addition of 38% strength hydrochloric acid. 1900 ml of THF and 94.1 g (0.93 mol) of triethylamine are subsequently added and the pH increases to 10. At 10° C., 60 g (0.365 mol) of 3-isobutoxyacryloyl chloride are subsequently added dropwise over a period of 7 minutes. The mixture is stirred at the same temperature for 28 minutes, and a further 17 g (0.103 mol) of 3-isobutoxyacryloyl chloride are then added over a period of 29 minutes. For work-up, the phases are separated and the lower phase is extracted with 2 l of THF. The collected organic phases are combined and the solvent is distilled off under reduced pressure. This gives 78.3 g of intermediate which is dissolved in 625 g of 10% strength sulfuric acid. The reaction mixture is heated at 90° C. for 70 minutes. Gas chromatographic analysis of the reaction mixture showed a yield of 64% (based on 3-isobutoxyacryloyl chloride). Isomer ratio: ≧100:1

Using the processes described above, the compounds below were prepared in a similar manner.

| Constitution | Physical data; 1H NMR data |
|---|---|
| N-ethyl pyrazole-OH (Et) | m.p. 94° C.<br>1H NMR(d6-DMSO): 1.3(t, 3H), 3.9(q, 2H), 5.3 (d, 1H), 7.3(d, 1H), 10.4(brd., 1H). |
| N-nPr pyrazole-OH | b.p.(1 mbar): 114° C.<br>1H NMR(d6-DMSO): 0.8(t, 3H), 1.6(m, 2H), 3.7(t, 2H), 5.3(d, 1H), 7.0(d, 1H). |
| N-nBu pyrazole-OH | b.p.(0.5 mbar): 107–108° C.<br>1H NMR(d6-DMSO): 0.9(t, 3H), 1.2(m, 2H), 1.7(m, 2H), 3.8(t, 2H), 5.2(d, 1H), 7.0(d, 1H), 9.1(brd., 1H). |

| Constitution | Physical data; 1H NMR data |
|---|---|
| 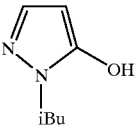 iBu | b.p.(2 mbar): 135° C.<br>1H NMR(d6-DMSO): 0.9(d, 6H), 2.1(sept., 1H), 3.5(d, 2H), 5.2(d, 1H), 7.0(d, 1H), 10.6 (brd., 1H). |
| 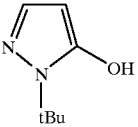 tBu | 1H NMR(d6-DMSO): 1.5(s, 9H), 5.3(d, 1H), 7.0(d, 1H), 10.6(brd., 1H). |
| 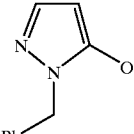 Ph | 1H NMR(d6-DMSO): 5.1(s, 2H), 5.3(s, 1H), 7.1–7.3(m, 6H), 11.1(brd., 1H). |
| 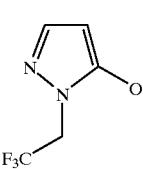 F₃C | 1H NMR(d6-DMSO): 4.7(q, 2H), 5.4(d, 1H), 7.3(d, 1H9, 11.4(brd., 1H). |
| 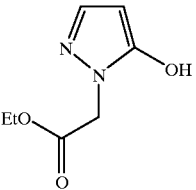 EtO | 1H NMR(d6-DMSO): 1.2(t, 2H), 4.1(q, 2H), 4.7 (s, 2H), 5.3(d, 1H), 7.2(d, 1H), 11.2(brd., 1H). |
| 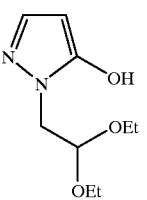 | 1H NMR(d6-DMSO): 1.0(t, 6H), 3.3(m, 2H), 3.6 (m, 2H), 3.9(d, 2H), 4.7(t, 1H), 5.3(d, 1H), 7.1 (d, 1H), 11.0(brd., 1H). |
| 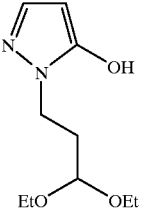 | 1H NMR(d6-DMSO): 1.1(t, 6H), 1.9(m, 2H), 3.4(m, 2H), 3.6(m, 2H), 3.9(m, 2H), 4.5(m, 1H), 5.3(d, 1H), 7.1(d, 1H), 11.0(brd., 1H). |

The 1-substituted 5-hydroxypyrazoles prepared by the process according to the invention are useful precursors for preparing, for example, crop protection agents, such as herbicides. Herbicides disclosed in WO 96/26206 are, for example,

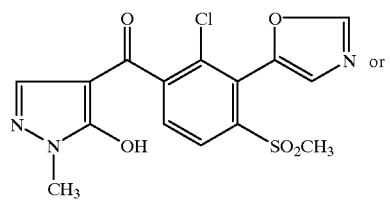

-continued

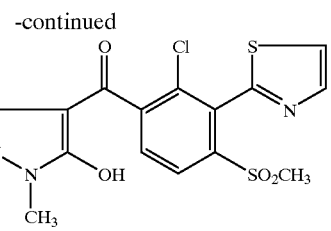

We claim:
1. A process for preparing a 1-substituted 5-hydroxypyrazole of the formula I

I

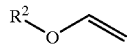

in which $R^1$ is $C_1$–$C_6$-alkyl, $C_2$–$C_6$-alkenyl, $C_2$–$C_6$-alkynyl, $C_3$–$C_6$-cycloalkyl or $C_1$–$C_4$-alkoxy, where these groups may be substituted by halogen, $C_1$–$C_4$-alkoxy, phenoxy, $C_1$–$C_6$-alkoxycarbonyl, $C_1$–$C_6$-alkylthiocarbonyl or by a cyclic ring system having 3–14 ring atoms, which comprises a) reacting an alkyl vinyl ether of the formula III

III

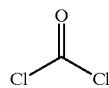

in which $R^2$ is $C_1$–$C_6$-alkyl or $C_3$–$C_6$-cycloalkyl with phosgene IVa, "diphosgene" IVb or "triphosgene" IVc IVa

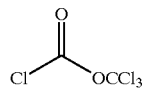

IVb

IVc

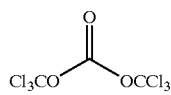

to give an acyl chloride of the formula V

V

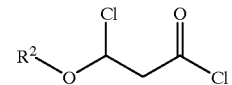

b) converting this by elimination of hydrogen chloride into the corresponding 3-alkoxyacryloyl chloride of the formula VI

VI

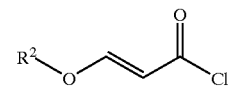

and c) reacting this with a hydrazine of the formula VII

VII

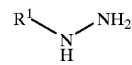

in which $R^1$ is as defined above to give a 5-hydroxypyrazole of the formula I.

2. A process as claimed in claim 1, wherein the reaction in step a) is carried out at from −78° C. to 100° C.

3. A process as claimed in claim 1, wherein the alkyl vinyl ether III is reacted with phosgene IVa, diphosgene IVb or triphosgene IVc in a molar ratio of from 0.1:1 to 1:1.

4. A process as claimed in claim 1, wherein the reaction in step b) is carried out at from 30° C. to 80° C.

5. A process as claimed in claim 1, wherein the reaction in step c) is carried out at from −20° C. to 80° C.

6. A process as claimed in claim 1, wherein the 3-alkoxyacryloyl chloride VI is reacted with a hydrazine VII at from −20° C. to 50° C. to give a hydrazide which is subsequently cyclized in the presence of an organic or inorganic acid at from 30 to 100° C.

7. A process as claimed in claim 6, wherein the inorganic acid used is sulfuric acid, hydrochloric acid or phosphoric acid.

* * * * *